United States Patent [19]

Young et al.

[11] Patent Number: 5,031,458
[45] Date of Patent: Jul. 16, 1991

[54] PORTABLE ULTRASONIC INSPECTION PROBE FOR LAMINATED STRUCTURES

[75] Inventors: Fred D. Young, Bellevue; James E. Cook, Seattle, both of Wash.

[73] Assignee: The Boeing Company, Seattle, Wash.

[21] Appl. No.: 371,347

[22] Filed: Jun. 26, 1989

Related U.S. Application Data

[63] Continuation-in-part of Ser. No. 53,346, May 22, 1987, Pat. No. 4,848,159.

[51] Int. Cl.$^5$ ............................................. G01N 29/04
[52] U.S. Cl. ..................................... 73/636; 73/618; 73/633; 73/641
[58] Field of Search ............... 73/636, 635, 633, 620, 73/618, 641

[56] References Cited

U.S. PATENT DOCUMENTS

| | | | |
|---|---|---|---|
| 2,951,365 | 9/1960 | Legrand | 73/636 |
| 3,028,751 | 4/1962 | Joy | 73/634 |
| 3,121,325 | 2/1964 | Rankin et al. | 73/635 |
| 3,382,707 | 5/1968 | Heselwood | 73/638 |
| 3,616,683 | 11/1971 | Pachurka | 73/635 |
| 3,616,684 | 11/1971 | Nusbickel | 73/635 |
| 3,850,028 | 11/1974 | Thompson et al. | 73/643 |
| 3,999,423 | 12/1976 | Tyree | 73/635 |
| 4,143,553 | 3/1979 | Martens et al. | 73/641 |
| 4,165,648 | 8/1979 | Pagano | 73/625 |
| 4,235,112 | 11/1980 | Kaiser | 73/634 |
| 4,487,071 | 12/1984 | Pagano et al. | 73/612 |
| 4,593,569 | 6/1986 | Joy | 73/636 |
| 4,700,574 | 10/1987 | Turbe | 73/636 |

Primary Examiner—Hezron E. Williams
Assistant Examiner—Rose M. Finley
Attorney, Agent, or Firm—Christensen, O'Connor, Johnson & Kindness

[57] ABSTRACT

A portable ultrasonic inspection probe (400) for determining the presence, location, and size of flaws in a laminated structure such as a composite "I" stiffener (30'). The probe includes a shoe assembly (402) having a plurality of shoes (52', 54', 56', 58') that are arranged for coordinated movement relative to the "I" stiffener and house a plurality of ultrasonic transducers that produce inspection information related to the "I" stiffener. The shoes are biased by spring assemblies (64' and 66') toward the web 34' and flange 32' and flange 32' of the "I" stiffener. A fore drive (404) and an aft drive (406) are mounted on the shoe assembly and spring loaded to engage the "I" stiffener so as to cause translational movement of the shoe assembly when energized. The shoe assembly may be moved by either one or both of the drives. A position encoder (408) produces information related to the position of the probe as it is moved along the "I" stiffener. The position encoder is spring loaded such that it is driven by the relative motion of the "I" stiffener when the fore drive engages the "I" stiffener and by the fore drive when the fore drive does not engage the "I" stiffener.

24 Claims, 4 Drawing Sheets

PORTABLE ULTRASONIC INSPECTION PROBE FOR LAMINATED STRUCTURES

CROSS-REFERENCE TO RELATED APPLICATION

This application is a continuation-in-part of U.S. Ser. No. 07/053,346, filed May 22, 1987, now U.S. Pat. No. 4,848,159, and entitled "Ultrasonic Inspection Probe For Laminated Structures," the subject matter of which is incorporated herein by reference.

FIELD OF THE INVENTION

The present invention relates in general to ultrasonic inspection and, more particularly, to the use of ultrasonic transducers to detect and size flaws in laminated composite or other structures.

BACKGROUND OF THE INVENTION

The use of composites for aircraft structures has experienced a significant growth in recent years. Such structures are typically formed by curing or consolidating multiple layers of graphite/epoxy or other fiber resin composite materials into a laminate of desired configuration. As fabrication techniques have improved, it has become possible to produce large-scale composite panels having stiffeners integrally molded thereto. These stiffeners have been variously shaped, ranging from simple plate-like blades to angled structures having a T, I, L, or Z cross-sectional configuration.

Heretofore, composite structures have been principally inspected with a hand-scanning method in which a handheld yoke, carrying either through-transmission or pulse echo transducers, is manipulated by hand over the part under study. While the hand-scan methods have been successfully used to locate flaws in composite structures, they have not been entirely satisfactory. For example, since the technique is dependent upon the freehand guidance of the yoke by the operator, the technique is inherently slow and unreliable since there is no assurance that there will be 100% coverage of the part under inspection. In addition, since the operator must simultaneously manipulate the yoke and observe and analyze a displayed output of the ultrasonic transducers, it is difficult to accurately and reliably identify and locate flaws.

Another type of prior art inspection device is an ultrasonic probe that is designed to be held and manipulated by a multi-axis gantry robot. An example of such a device is described in U.S. Pat. No. 4,848,159, the parent of this application. This probe/robot combination is particularly well suited for use in a production mode to inspect large laminated structures, such as aircraft wing assemblies. Unfortunately, gantry robots of the sort necessary to manipulate an ultrasonic probe are large and cumbersome, which makes them impractical to use with a "portable" type of probe that is intended to be moved about a production facility or into the field. Further, this probe/robot combination is best suited for inspecting a laminated structure, such as a stiffener, along its entire length, as opposed to inspecting just an intermediate portion thereof. This is due, in part, to the programming used to control the gantry robot. Lastly, gantry robots are expensive to purchase and require a substantial amount of maintenance.

Another type of prior art ultrasonic inspection probe requires the use of a "mouse" or mechanical crawler to pull the probe along the part under inspection. This probe/crawler combination is better suited for use as a portable probe than the probe/robot combination discussed above. Unfortunately, however, the crawler requires the additional use of costly run-on and run-off equipment at the beginning and end of each part being inspected.

As can be appreciated from the foregoing discussion, there has developed a need for an inexpensive, portable ultrasonic inspection probe that does not require extensive auxiliary equipment for its operation. Such a portable probe could be moved about a production facility and used wherever a part that needs to be inspected is located. Further, such a portable probe could be used outside the production facility to inspect in-service parts. In addition, such a portable probe should be equally well suited for inspecting only an intermediate portion of a part, e.g., a stiffener, as well as the entire part. Also, the portable probe should be sized to allow closely spaced parts to be inspected. This invention is directed to a portable ultrasonic inspection probe that achieves these results.

SUMMARY OF THE INVENTION

In accordance with the present invention, there is provided a portable inspection probe for determining the presence, location, and size of flaws in the radius region and adjacent areas of a structure. The portable probe comprises: a shoe assembly having a plurality of transducers; a first drive and a second drive; and, a position encoder. The shoe assembly further comprises a plurality of individual shoes configured for complementary engagement with the structure under inspection. The individual shoes are biased toward each other by spring assemblies so as to clamp the laminated structure therebetween. The plurality of transducers inspect the laminated structure and produce relevant inspection information. The first and second drives are mounted to the shoe assembly and create translational movement of the probe along the structure. The position encoder provides probe position information as the probe is moved along a structure. The position information allows the inspection information to be keyed to the position of the probe so that a user can determine that 100% coverage of the structure under inspection has occurred.

In accordance with further aspects of the present invention, the first and second drives and the position encoder are biased toward the structure under inspection. Preferably, the first and second drives are rigidly mounted to one shoe of the shoe assembly, which is biased toward the structure by the spring assemblies. The position encoder is pivotally mounted to one shoe of the shoe assembly and biased away from the shoe toward the structure.

In accordance with still further aspects of the present invention, the first and second drives operate synchronously. The probe is moved along the structure when only the first drive engages the structure and when only the second drive engages the structure and when both the first and second drives engage the structure. The position encoder engages the structure and is driven by the relative motion of the structure when the first drive engages the structure and moves the shoe assembly. The position encoder engages the first drive and is driven by the first drive when the probe is moved by the second drive and the first drive does not engage the structure.

As will be appreciated from the foregoing summary, the invention provides a portable ultrasonic inspection probe for determining the presence, location, and size of flaws in a structure.

BRIEF DESCRIPTION OF THE DRAWINGS

The foregoing and other features and advantages of the invention will become more readily appreciated as the same becomes further understood by reference to the following detailed description when taken in conjunction with the accompanying drawings, wherein.

DETAILED DESCRIPTION OF THE PREFERRED EMBODIMENT

There has developed a need for an inexpensive portable ultrasonic inspection probe that does not require auxiliary equipment, such as gantry robots and mechanical crawlers, for use in inspecting laminated composite or other structures. Such a portable probe should be suited for use in both a production facility to inspect large and small structures (or parts), as well as outside the production facility to inspect in-service parts. Further, the portable probe should be equally well suited for inspecting intermediate portions as well as parts in their entirety. The present invention is a portable probe designed to accomplish these results.

Ultrasonic inspection probes are well known by those familiar with the composite or laminated structure art. An example of such a probe is described in a U.S. patent application entitled "Ultrasonic Inspection Probe For Laminated Structures," Ser. No. 053,346, filed on May 22, 1987 now U.S. Pat. No. 4,848,159, by Kennedy et al. The disclosure of U.S. Ser. No. 053,346, and particularly the information relating to the probe shoes, including the ultrasonic transducers, the internal conduits, and the biasing spring assemblies is hereby incorporated by reference.

Figure 1:
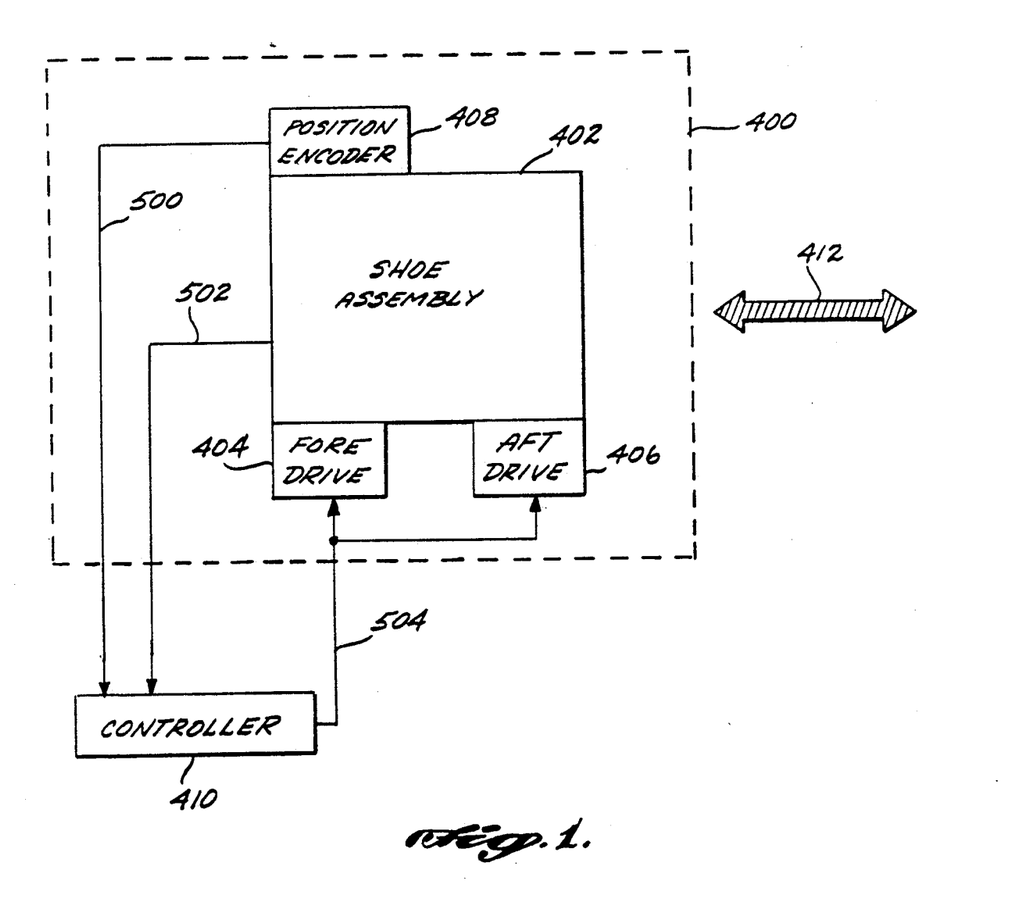
FIG. 1 is a block diagram of a portable ultrasonic inspection probe formed in accordance with the present invention.

Turning now to FIG. 1, there is illustrated a block diagram of a portable ultrasonic inspection probe 400 formed in accordance with the present invention. The portable probe 400 includes: a shoe assembly 402; a fore drive 404; an aft drive 406; and, a position encoder 408. The shoe assembly 402 carries a plurality of transducers used to inspect a laminated structure (not shown in FIG. 1). In one physical embodiment of the portable ultrasonic inspection probe 400, the shoe assembly 402 is similar to an upper flange/web shoe assembly (62) described in parent application, U.S. Pat. No. 4,848,159, noted above. That is, the shoe assembly 402 includes multiple shoes, transducers, internal conduits, and spring assemblies as configured in the upper flange/web shoe assembly of the parent application. It is to be understood, however, that other shoe arrangements are equally well suited for use with the portable probe 400 of the present invention.

The fore drive 404 and the aft drive 406 operate cooperatively to move the shoe assembly 402 along the part under test. The direction of movement of the shoe assembly 402 and, hence, the probe 400, is indicated schematically in FIG. 1 by a double directional arrow 412. Both the fore and aft drives 404 and 406 move the probe 400 in either direction indicated by the direction arrow 412. More specifically, both the fore and aft drives 404 and 406 may move the probe 400 forward (e.g., to the left in FIG. 1) and backward (e.g., to the right in FIG. 1). Further, the probe 400 can be moved either forward or backward by either one or both of the drives 404 and 406.

The position encoder 408 produces information related to the position of the probe 400 as the probe 400 is moved along the part being inspected. This encoded position information is provided on line 500. Similarly, transducers in the shoe assembly 402 produce ultrasonic inspection information, such as pulse echo and through-transmission data, and provide this information on line 502.

A remote controller 410, which does not form part of the present invention, receives and analyzes the encoded position information on line 500 and the inspection information on line 502 to determine the presence, position, and size of flaws in the part under inspection. The controller 410 also controls the fore and aft drives 404 and 406. In accordance with the preferred embodiment of the invention, the controller 410 produces and applies a common drive control signal to both drives 404 and 406 via line 504. As stated above, the drives 404 and 406 work cooperatively to move the probe 400 along the part under inspection. That is, the drives 404 and 406 operate synchronously (i.e., at the same speed and in the same direction) to move the probe.

Figure 2:
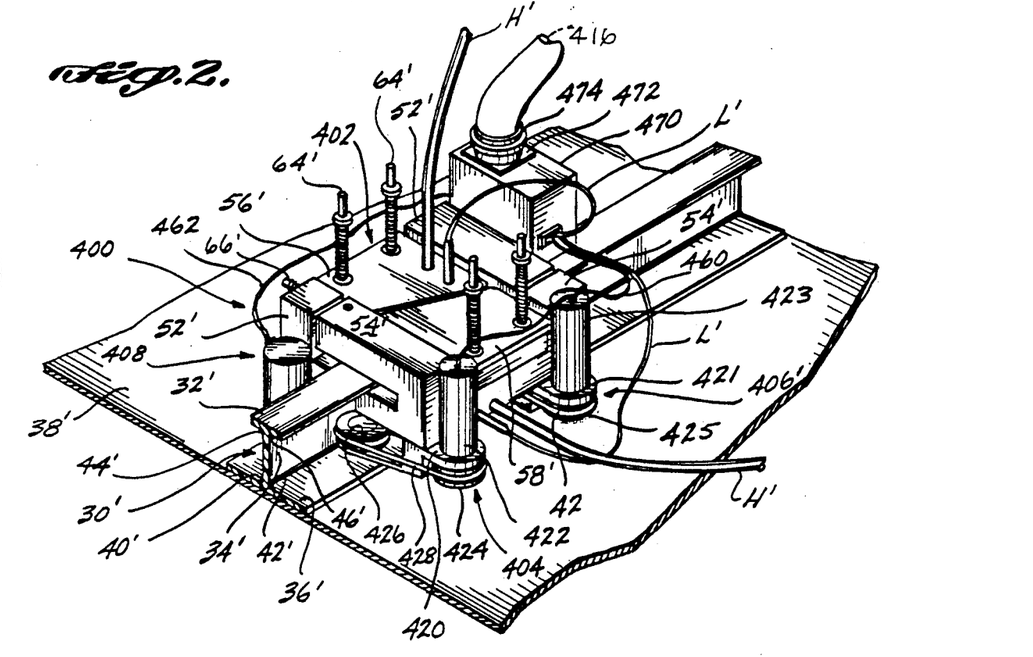
FIG. 2 is a simplified isometric view of the presently preferred embodiment of the portable ultrasonic inspection probe depicted in FIG. 1.

FIG. 2 is a detailed illustration of a portable probe 400 of the type shown in block form in FIG. 1 applied to a part under test. In the discussion which follows, elements that are the same or substantially the same as elements described in the parent application (U.S. Ser. No. 053,346 now U.S. Pat. No. 4,848,159) are given the same reference numbers, but are distinguished therefrom with a prime symbol ('). Since, as noted above, the disclosure of the parent application is incorporated by reference, the details of these common elements are not discussed herein.

The part, or laminated structure, under test depicted in FIG. 2, comprises an "I" stiffener 30' integrally molded to a skin panel 38'. The stiffener 30' has an upper flange 32', a web 34', and a lower flange 36'. The web 34' is substantially orthogonal to the upper and lower flanges 32' and 36'. Radii 40', 42', 44', and 46' are formed at the juncture of the web 34' and the upper and lower flanges 32' and 36'. Only a "T"-shaped portion of the "I" stiffener 30', consisting of the upper flange 32', web 34', and radii 44' and 46' formed at the juncture of the upper flange 32' and the web 34' are inspected by the illustrated embodiment of the probe 400.

The shoe assembly 402 of the present invention is substantially the same as the upper flange/web shoe assembly described in U.S. Pat. No. 4,848,159. This shoe assembly 402 comprises: left and right top shoes 56' and 58'; and, left and right flange shoes 52' and 54', respectively. The shoes 52'–58' include a plurality of ultrasonic transducers (omitted in FIG. 2 for purposes of clarity). Just as with the upper flange/web shoe assembly of the parent application, the four shoes 52′-58′ of the shoe assembly 402 of the present invention are spring-loaded to cooperatively engage the "I" stiffener 30′. More specifically, the left and right flange shoes 52′ and 54′ are located on opposite sides of the "I" stiffener 30′ and biased toward one another and, thus, the web 34′, by spring assemblies 66′. Similarly, the left and right top shoes 56′ and 58′ are formed of pieces that are biased toward the upper flange 32′ by spring assemblies 64′. Further, the shoes 52′-58′ are interconnected to one another so as to form an integral assembly. Each of the shoes 52′-58′ has a water supply hose, designated H′, and an electrical lead, designated L′, connected thereto. L′ and H′ are intended to pictorially illustrate that there is an electrical connector running to each one of the plurality of transducers in the shoes and that there is a plurality of hoses through which water (or other suitable couplant) is supplied to internal conduits within the shoes. Since a thorough discussion of the shoes 52′-58′, including: the ultrasonic transducers; the spring assemblies; and the hose and electrical lead connections is presented in the parent application, Ser. No. 053,346 now U.S. Pat. No. 4,848,159, which do not, per se, form part of this invention, the details of these elements are not discussed here.

As further illustrated in FIG. 2, and as will be discussed more fully below, the fore drive 404 and the aft drive 406 are mounted on the shoe assembly 402. More particularly, the drives 404 and 406 are mounted on the right flange shoe 54′. As oriented in FIGS. 2 and 3, the fore drive 404 is located near the left end of the shoe assembly 402 and the aft drive 406 is located near the right end of the shoe assembly 402. For purposes of discussion, movement of the shoe assembly 402 to the left is forward movement and movement to the right is rearward movement. Accordingly, the left end of the shoe assembly 402 is the forward end and the right end of the shoe assembly is the rear, or aft end, hence the terms fore and aft drives 404 and 406.

The fore drive 404 comprises: a base 420; a motor 422; a motor drive wheel 424; an idler wheel 426; and, a motor drive belt 428. The base 420 is an elongated, generally flat piece of rigid material having a z-shape when viewed in elevational cross-section. See FIG. 4. The central area 420a of the base 420 is rigidly attached to the right flange shoe 54′. One leg 420b of the base 420 extends inwardly towards the "I" stiffener 30′ at one end and the other leg 420c extends outwardly away from the "I" stiffener 30′ on the other end. The upper surface of the inwardly extending leg 420b is spaced from the lower surface of the right shoe flange 54′. As oriented in FIG. 2, the motor 422 is vertically mounted to the top of the outwardly extending leg 420c of the base 420, such that the motor shaft (not shown) passes vertically through the base 420. The motor drive wheel 424 is mounted on the motor shaft, below the outwardly extending leg 420c of the base 420. The idler wheel 426 is rotatably mounted on the upper surface of the inwardly extending leg 420b of the base 420, in the space between the inwardly extending leg and the lower surface of the right shoe flange 54′. The motor drive belt 428 couples the drive wheel 424 to the idler wheel 426.

Similarly, the aft drive 406 comprises: a base 421; a motor 423; a motor drive wheel 425; an idler wheel 427; and, a motor drive belt 429. The configuration of components of the aft drive 406 is substantially the same as the configuration components of the fore drive 404 described above, and, hence is not repeated below.

In one physical embodiment of the probe 400, the belts 428 and 429 are O-rings sized to extend beyond the periphery of the drive and idler wheels. In this embodiment, the motors 422 and 423 are preferably DC motors capable of moving (in the manner described below) the probe 400 along the "I" stiffener 30′ at a speed of at least 5 inches/second in both forward and reverse directions.

Figure 3:
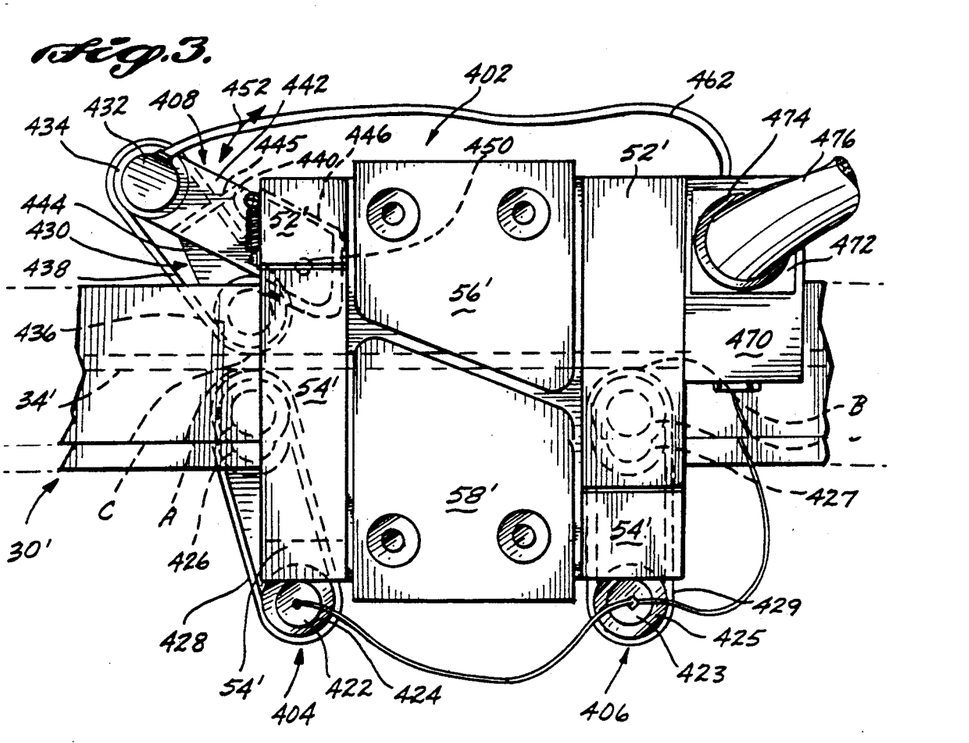
FIG. 3 is a top view of the probe depicted in FIG. 2.

As noted above, and further described in the parent application, Ser. No. 053,346 now U.S. Pat. No. 4,848,159, the shoe assembly 402 is spring-loaded into the "I" stiffener 30′. Accordingly, the right flange shoe 54′ and, hence, the fore and aft drives 404 and 406 are also spring-loaded into the "I" stiffener 30′. The idler wheels 426 and 427 are positioned such that the spring loading causes the motor drive belts 428 and 429 to contact the web 34′ at a point where the belts 428 and 429 pass around their respective idler wheels 426 and 427. These points of contact, denoted A for the fore drive 404 and denoted B for the aft drive 406, are best depicted in FIG. 3. Control signals from the remote controller 410 (see FIG. 1) are applied to the drives 404 and 406 via line 504, which is represented in FIG. 2 as a wire 460. When the appropriate control signal is applied to the drives 404 and 406, the motors 422 and 423 drive the respective drive wheels 424 and 425, which drive the associated motor drive belts 428 and 429. Driving the belts 426 and 427 causes translational movement of the probe 400 along the "I" stiffener 30′ due to the friction between the belts 426 and 427 and the web 34′ of the "I" 30′. As briefly noted above and as will become better understood from the following discussion, the probe 400 may be driven by either one, or both, of the drives 404 or 406.

As best illustrated in FIG. 3, the fore drive 404 is oriented differently than the aft drive 406 with respect to the shoe assembly 402. The fore drive 404 diverges from the right flanges shoe 54′. The angle of divergence is such that the idler wheel 426 of the fore drive 404 is positioned forward of the motor drive wheel 424 and, more particularly, forward of the left, or forward, edge of the shoe assembly 402. Contrariwise, the aft drive 406 is mounted square with the shoe assembly, i.e., such that the aft drive is inside the right, or rearward, edge of the shoe assembly 402. The significance of this orientation of the fore and aft drives 404 and 406 is discussed more fully below. Briefly, however, when the probe 400 is placed at the beginning of a part to be inspected, the fore drive begins moving the shoe assembly 402 in the forward (i.e., left) direction before the transducers (in the shoes 52′-58′) begin inspecting the part. Likewise, the aft drive 404 moves the transducers in the shoe assembly 402 completely off the end of the part. As a result, the entire length of the part may be inspected without the use of auxiliary run-on and run-off equipment, as is required by some prior art probes.

The position encoder 408 generates probe position information as the probe 400 moves along the "I" stiffener 30′ and supplies the position information to the controller 410 via line 500, which is depicted in FIG. 2 as a wire 462. As will become better understood from the following discussion, like the fore and aft drives 404 and 406, the encoder 408 is spring-loaded into the web 34′. However, the way in which the position encoder 408 is spring-loaded into the web 34′ is different from the way the drives 404 and 406 are spring-loaded into the web.

Figure 4:
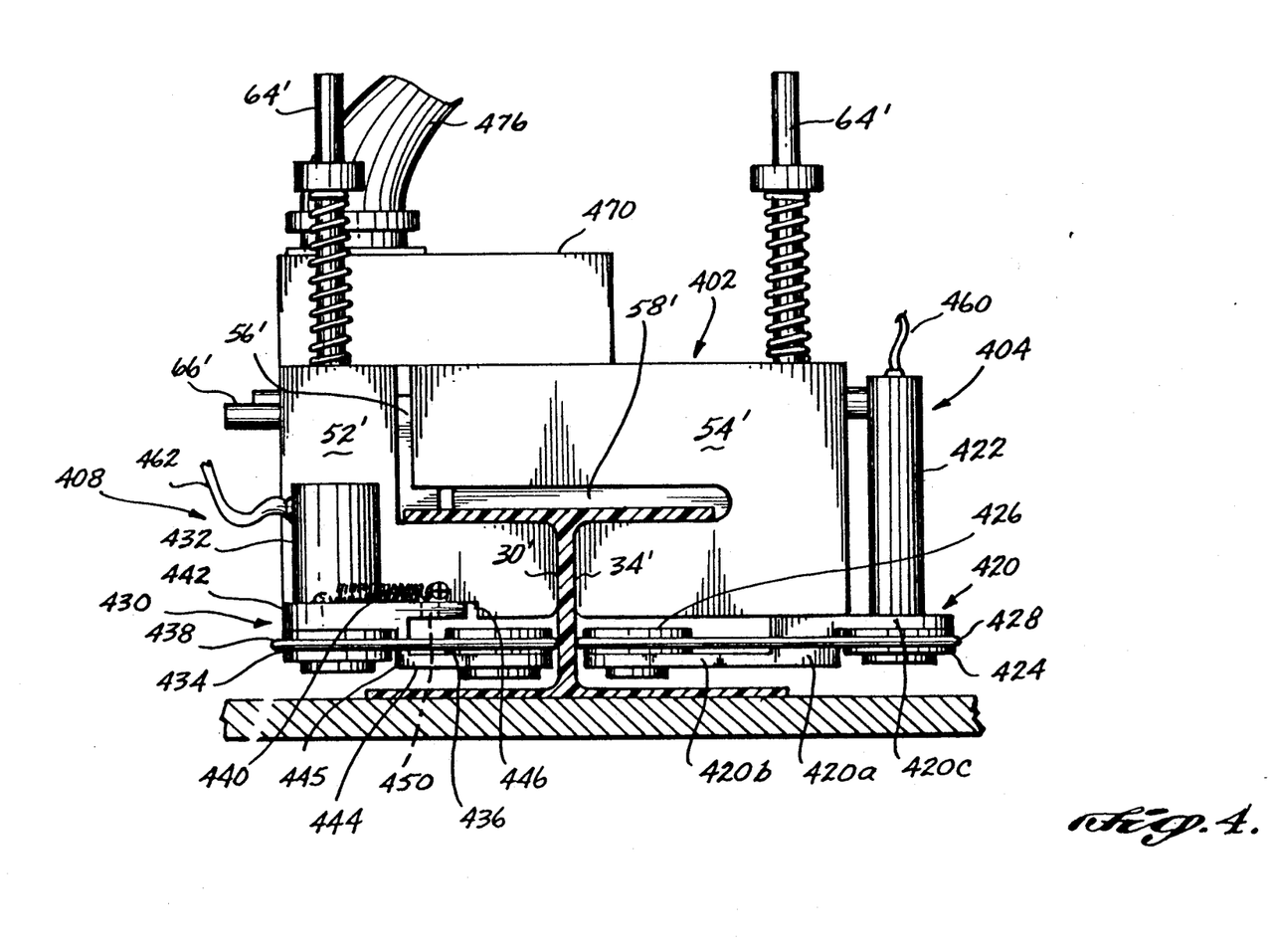
FIG. 4 is a front elevational view of the probe depicted in FIG. 2.

The position encoder 408 includes a shaft encoder 432 and a position encoder mounting and drive mechanism that is best illustrated in FIGS. 3 and 4. As best depicted in FIG. 3, the position encoder mounting and drive mechanism comprises: a base 430; a driven wheel 434; an encoder drive wheel 436; an encoder drive belt 438; and, a spring 440. In one physical embodiment of the invention, the base 430 is made of rigid material and includes two vertically spaced apart legs 442 and 444 connected by a connecting member 445. As oriented in FIG. 3, leg 442 is located above leg 444 and is displaced from leg 444 by an acute angle of about 25 degrees (25°). The outer end of the legs 442 is pivotally mounted to the underside of the left flange shoe 52' at point 450. Preferably, this leg 442 is positioned within a channel 446 formed in the underside surface of the left flange shoe 52' that is wider than the width of the first leg 442. Thus, the first leg 442 and the base 430 are free to rotate to a limited extent about point 45°, as depicted by an arrow 452.

The upper surface of the other leg 444 is spaced from the lower surface of the left flange shoe 52'. The shaft encoder 432 is vertically mounted atop the first leg 442, near where the legs are joined. The shaft of the encoder 432 passes through this other end of the first leg 442. The driven wheel 434 is mounted on the shaft of the encoder 432 below the first leg 442. The end of the other or second leg 444 is connected to the first leg 442, via the connecting member 445, at an intermediate location between the ends of the first leg 442. The drive wheel 436 is rotatably mounted atop the outer end of the second leg 444 in the space between the second leg 444 and the lower surface of the left flange shoe 52'. The length of the second leg 444 is such that the periphery of the drive wheel 436 is adjacent to the web 34' of the "I" stiffener 30'. The driven wheel 434 is coupled to the drive wheel 436 by the encoder drive belt 438. This configuration of the position encoder 408 is further illustrated in FIG. 4. In one actual embodiment of the probe 400, as with the fore and aft drives 404 and 406, the encoder drive belt 438 is an O-ring sized to extend beyond the outer periphery of the drive and driven wheels. In this embodiment, the shaft encoder 432 is an optical encoder that generates position information in the form of pulses, which are accumulated and decoded by the controller 410 (FIG. 1).

As noted above, and further depicted in FIG. 3, the position encoder 408 is spring-loaded into the web 34' by the spring 440. One end of the spring 440 is connected to the left flange shoe 52' and the other end is connected to the first leg 442 of the base 430. The connection points are such that the spring 440 bias force keeps the belt 438 in contact with the web 34' as the belt 438 passes over the encoder drive wheel 436. The point of contact is denoted C in FIG. 3. As will become better understood from the following discussion, the spring 440 also urges the position encoder drive belt 438 into contact with the fore drive belt 428 when the position encoder 408 and the fore drive 404 have moved off the end of the "I" stiffener 30'. Because the fore drive 404 continues to rotate synchronously with the aft drive 406, even after the fore drive leaves the web, this belt coupling causes the position encoder 408 to continue to produce position information after the free drive 404 leaves the web 34'. Preferably, the position encoder 408 continues to produce position information until the aft drive 406 moves off the "I" stiffener 30'.

As best depicted in FIGS. 2 and 3, the probe 400 also includes an electrical terminal box 470. In one physical embodiment of the invention, the terminal box 470 is mounted to the left flange shoe 52'. The wire 460 from the fore and aft drives 404 and 406 and the wire 462 from the shaft encoder 432 are routed into the box 470. The leads, L', from the transducers are also routed into the box 470. The box 470 preferably includes a receptacle 472 suitable for receiving a multi-pin plug 474 attached to a multiple conductor cable 476. The wires 460 and 462 and the leads, L', are connected to the receptacle 472. The cable 476 is connected on the other end to the controller 410.

As previously discussed, the probe 400 is moved along an "I" stiffener 30' by one or both of the drives 404 and 406. As was also noted above, the position encoder 408 is spring-loaded to engage either the web 34' or the fore drive 404, depending upon the position of the probe 400 along the "I" stiffener 30'. As a result, encoded position information and inspection information are provided for the entire length of the "I" stiffener 30'. These features of the probe 400 are best illustrated in FIGS. 5A through 5D, and are discussed in more detail next.

Figure 5A:
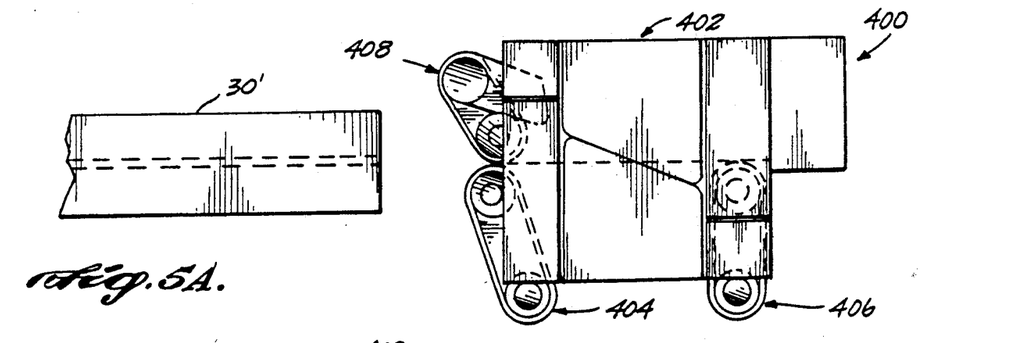
FIGS. 5A through 5D are a sequence of top views of the probe depicted in FIG. 2 illustrating the probe as it moves along a laminated structure under inspection.
Figure 5B:
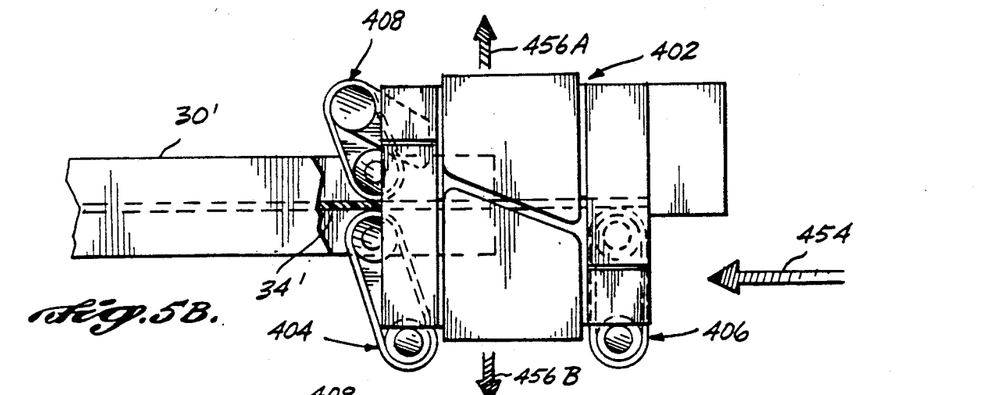

FIG. 5A shows the position of the various elements of the probe 400 before the probe has moved onto the "I" stiffener 30'. In this position, the various shoes of the shoe assembly 402 are urged together and the belt 438 of the position encoder 408 engages the belt 428 of the fore drive 404. As depicted in FIG. 5B, when the probe 400 is moved onto the "I" stiffener 30', the shoes of the shoe assembly 402 are urged apart by the web 34'. The outward movement of the shoes is depicted by direction arrows 456A and 456B. In this position, the belts 428 and 438 of the fore drive 404 and the position encoder 408 engage the web 34'. At this point the probe 400 is being moved along the stiffener 30' by the fore drive 404. The position encoder 408 produces position information because its drive belt 438 is being moved by frictional engagement with the web 34' of the "I" stiffener 30'. The direction of movement of the probe 400 along the "I" stiffener 30' is indicated by direction arrow 454. At this position along the "I" stiffener 30', the aft drive 406 is not engaging the web 34'. However, since the fore and aft drives 404 and 406 operate synchronously, the aft drive 406 is driving the associated belt 428.

Figure 5C:
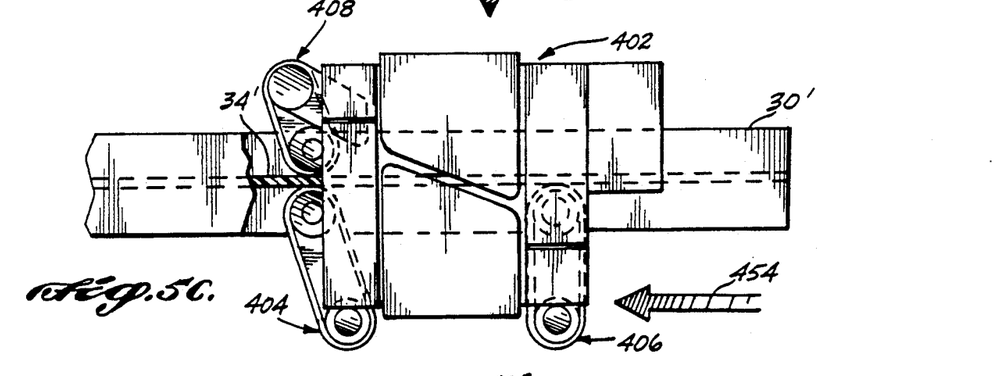

The fore drive 404 eventually moves the probe 400 along the stiffener 30' to the point where the aft drive 406 engages the web 34'. This position is depicted in FIG. 5C. The probe 400 is now moved along the "I" stiffener by both drives 404 and 406. The position encoder 408 continues to engage the web 34' and, thus, continues to produce position information.

Figure 5D:
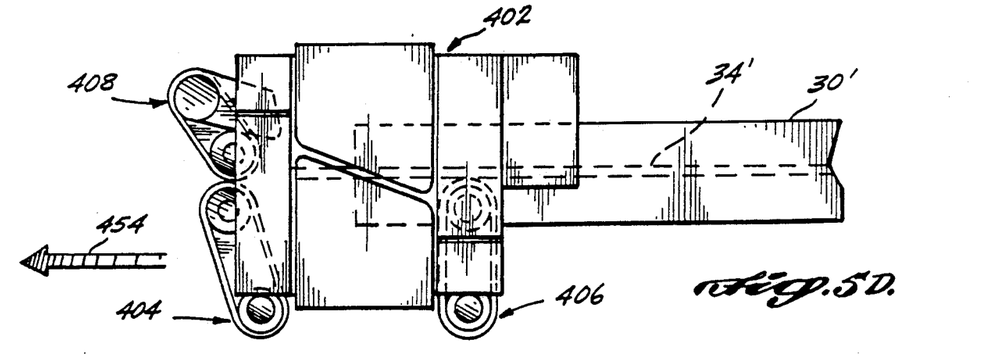

When the probe 400 reaches the other end of the stiffener 30', the fore drive 404 moves off of and no longer engages the web 34'. See FIG. 5D. Thereafter, the probe 400 continues to be moved along the "I" stiffener 30' by the aft drive 406. FIG. 5D also shows, as discussed above, that the belt 438 of the position encoder 408 is urged into contact with the belt 428 of the fore drive 404 by the action of the spring 440 after the fore drive 404 leaves the web 34' of the "I" stiffener. Thus, the fore drive 404 continues to drive the position encoder 408, which continues to produce position information, as the aft drive 406 continues to move the probe 400 along the stiffener 30'. After the aft drive 406 moves past the end of the stiffener 30', the shoe assembly 402 of the probe 400 returns to the position depicted in FIG. 5A.

The fore and aft drives 404 and 406 and the spring-loaded position encoder 408 allow the portable ultrasonic inspection probe 404 to produce accurate position information along the entire length of the stiffener 30', while, at the same time, producing inspection information that is keyed to the position information. The orientation of these elements is such that the need for cumbersome and expensive run-on and run-off equipment, required by some of the prior art probes, is elminated. Further, the compact size of the probe 400 makes the probe 400 portable and simple to use in the field for inspecting in-service parts.

While the operation of the probe 400 has been discussed in terms of inspecting an "I" stiffener from end to end, it is to be understood that less than the entire length of a stiffener or other part can also be inspected. In this regard, the biasing arrangement of the shoe assembly 402, briefly noted above, and further discussed in the parent application, Ser. No. 053,346 now U.S. Pat. No. 4,848,159, permits the probe 400 to be placed on, and removed from, a stiffener at intermediate positions along the stiffener's length. To do so, an operator need simply urge the elements of the shoe assembly 402 apart so as to permit the probe 400 to slip over the upper flange of the stiffener. Removal of the probe 400 from an intermediate position of the stiffener is accomplished in a similar manner.

The use of two relatively small diameter wheels with each of the drives 404 and 406 and the position encoder 408, as opposed, for example, to using one large diameter wheel with each, allows the probe 400 to be placed on, and removed from, an intermediate point along the length of a stiffener forming part of a structure that includes other stiffeners or objects located close to the stiffener to be inspected. More specifically, the use of a single, larger diameter wheel mounted on the shafts of each of the drive motors 422 and 423 and position encoder 432 and sized to impinge on the web 34' at points A, B and C would increase the overall width of the probe 400, perhaps to the extent that the wheels would contact the adjacent stiffeners or objects before the shoes of the shoe assembly 402 can be urged apart a sufficient distance to clear the cap 32'. Thus, the use of single, larger diameter wheels may prevent placing the probe 400 onto, and removing it from, intermediate positions along the length of the "I" stiffener 30' in some instances. The two-wheel configuration of the preferred embodiment of the invention reduces this problem because the two-wheel configuration is narrower than such a single-wheel configuration. The narrower two-wheel configuration permits the "partial" inspection of the "I" stiffener 30' to be accomplished when other stiffeners (or objects) are closer to the stiffener to be inspected than would be the case with a single-wheel configuration because the narrower two-wheel configuration is not as wide when expanded to slip over the upper flange of a stiffener. This feature of the portable probe 400 of the present invention further increases the possible uses of the probe 400 for inspecting both production and in-service parts.

While a preferred embodiment of the invention has been illustrated and described, it is to be understood that, within the scope of the appended claims, various changes can be made. For example, the shoes of the shoe assembly and tranducers mounted therein can be arranged to inspect composite parts that intersect at angles other than 90 degrees. Further, the number of shoes, as well as their shape and arrangement can be different than as described. The fore and aft drives, as well as the position encoder could be arranged to engage the upper flange of an "I" stiffener. In addition, the position encoder could be rigidly mounted to the shoe assembly and the fore drive could be pivotally mounted and spring loaded to engage the position encoder. Further, the aft drive could be mounted at an angle relative to the shoe assembly similar to that of the fore drive. Other changes can also be made. Hence, it is to be understood that the invention can be practiced otherwise than as specifically described herein.

The embodiments of the invention in which an exclusive property or privilege is claimed are defined as follows:

1. A portable inspection probe for determining the presence, location, and size of flaws in a structure having a web and a flange, said probe comprising:
   (a) a shoe assembly having first and second ends, said shoe assembly including an aperture sized and shaped to receive the web and flange of a structure that includes a web and a flange, said shoe assembly including a plurality of shoes biased toward said aperture, said biased shoes being designed to have a plurality of transducers that produce flaw inspection information;
   (b) a first drive mounted on said shoe assembly, near said first end, for causing translational movement of said shoe assembly along the web and flange when the web and flange are positioned in said aperture in said shoe assembly;
   (c) a second drive mounted on said shoe assembly, near said second end, for causing translational movement of said shoe assembly along the web and flange when the web and flange are positioned in said aperture in said shoe assembly;
   (d) power means coupled to said first and second drives for synchronously energizing said first and second drives;
   (e) a position encoder mounted on said shoe assembly, near said first end, for producing position information relative to the position of said shoe assembly as said shoe assembly is moved by at least one of said first and second drives along the web and flange.

2. The probe of claim 1, wherein said shoe assembly is moved by said first drive when said first drive engages the structure and the web and flange are positioned in said aperture in said shoe assembly.

3. The probe of claim 2, wherein said first drive is designed to engage the web of the structure when the web and flange are positioned in said aperture in said shoe assembly.

4. The probe of claim 3, wherein said position encoder is designed (a) to engage the structure when the web and flange are positioned in said aperture in said shoe assembly and (b) to produce said position information as said shoe assembly is moved along the web and flange by said first drive.

5. The probe of claim 4, wherein said position encoder is designed to engage the web of the structure when the web and flange are positioned in said aperture in said shoe assembly.

6. The probe of claim 1, wherein said shoe assembly is moved by said second drive when said second drive engages the structure and the web and flange are positioned in said aperture in said shoe assembly.

7. The probe of claim 6, wherein said second drive is designed to engage the web of the structure when the web and flange are positioned in said aperture in said shoe assembly.

8. The probe of claim 7, wherein said position encoder is designed (a) to engage the structure when the web and flange are positioned in said aperture in said shoe assembly and (b) to produce said position information as said shoe assembly is moved by said second drive along the web and flange.

9. The probe of claim 8, wherein said position encoder is designed to engage the web of the structure when the web and flange are positioned in said aperture in said shoe assembly.

10. The probe of claim 6, wherein said position encoder is designed (a) to engage said first drive and (b) to produce said position information as a result of said engagement when said shoe assembly is moved by only said second drive.

11. A portable inspection probe for determining the presence, location, and size of flaws in a structure having a web and a flange, said probe comprising:
(a) a shoe assembly having a forward end and a rearward end, said shoe assembly including an aperture sized and shaped to receive the web and flange of a structure that includes a web and a flange, said shoe assembly including a plurality of shoes biased toward said aperture, said biased shoes being designed to house a plurality of transducers that produce flaw inspection information;
(b) a fore drive mounted on said shoe assembly, near said forward end, for causing translational movement of said shoe assembly in both forward and reverse directions along the length of the web and flange when the web and flange are positioned in said aperture in said shoe assembly;
(c) an aft drive mounted on said shoe assembly, near said rearward end, for causing translational movement of said shoe assembly in both forward and reverse directions along the length of the web and flange when the web and flange are positioned in said aperture in said shoe assembly;
(d) power means coupled to said fore and aft drives for synchronously energizing said fore and aft drives; and,
(e) a position encoder mounted on said shoe assembly for producing position information relative to the position of said shoe assembly as said shoe assembly is moved along the structure by at least one of said fore and aft drives.

12. The probe of claim 11, wherein said position encoder is located near said forward end of said shoe assembly.

13. The probe of claim 11, wherein each of said fore and aft drives comprises:
(a) a motor base rigidly mounted on said shoe assembly and having first and second ends;
(b) a motor mounted on said first end of said motor base, said motor having a shaft;
(c) a motor drive wheel mounted on the shaft of said motor;
(d) an idler wheel rotatably mounted on said second end of said motor base; and,
(e) a motor drive belt for coupling said motor drive wheel to said idler wheel by passing around the periphery of said motor drive wheel and said idler wheel, said idler and drive wheels positioned such that each said motor drive belt may be brought into frictional contact with the structure when the web and flange are positioned in said aperture in said shoe assembly so as to cause movement of said shoe assembly along said structure when said motor is energized.

14. The probe of claim 13, wherein each said motor drive belt may be brought into contact with the web of the structure when the web and flange are positioned in said aperture in said shoe assembly.

15. The probe of claim 13, wherein each said motor is a DC motor.

16. The probe of claim 15, wherein said motor in said fore drive and said motor in said aft drive are capable of moving said shoe assembly at a speed of at least 5 inches/second along the structure.

17. The probe of claim 13, wherein each said motor drive belt comprises at least one O-ring.

18. The probe of claim 11, wherein said position encoder includes:
(a) an encoder base having first and second ends, said first end of said encoder base being pivotally mounted on said shoe assembly;
(b) an encoder drive wheel rotatably mounted on said second end of said encoder base;
(c) a shaft encoder mounted on said encoder base between said first and second ends of said encoder base;
(d) a driven wheel mounted on a shaft of said shaft encoder; and,
(e) an encoder drive belt for coupling said encoder drive wheel to said driven wheel, said encoder drive belt being entrained around peripheral portions of said encoder drive wheel and said driven wheel, said encoder drive wheel being positioned such that movement of said shoe assembly along the structure when the web and flange are positioned in said aperture in said shoe assembly causes said encoder drive belt to frictionally engage said structure and rotate said driven wheel causing said shaft encoder to produce said position information.

19. The probe of claim 18, wherein said position encoder further comprises pivot means for pivotally mounting said encoder on said shoe assembly and biasing means for biasing said pivotally mounted position encoder toward said structure.

20. The probe of claim 19, wherein said biasing means is a coil spring having first and second ends, said first end being attached to said shoe assembly and said second end being attached to said encoder base.

21. The probe of claim 20, wherein said encoder drive belt is designed to frictionally engage the web of the structure at a point where said encoder drive belt passes around said peripheral portion of said encoder drive wheel.

22. The probe of claim 19, wherein said encoder drive belt frictionally engages said motor drive belt of said fore drive, such that when said shoe assembly is moved by only said aft drive, said motor drive belt of said fore drive rotates said encoder drive belt and causes said shift encoder to produce said position information.

23. The probe of claim 22, wherein said encoder drive belt and said motor drive belt of said fore drive engage at a point where said encoder drive belt passes around the periphery of said encoder drive wheel and where said motor drive belt of said fore drive passes around the periphery of said idler wheel of said fore drive.

24. The probe of claim 18, wherein said encoder drive belt is an O-ring.

* * * * *

UNITED STATES PATENT AND TRADEMARK OFFICE
CERTIFICATE OF CORRECTION

PATENT NO. : 5,031,458
DATED : July 16, 1991
INVENTOR(S) : F.D. Young et al.

It is certified that error appears in the above-identified patent and that said Letters Patent is hereby corrected as shown below:

| COLUMN | LINE | |
|---|---|---|
| 6 | 30 | ""I" 30'" should read --"I" stiffener 30'-- |
| 9 | 9 | "elminated" should read --eliminated-- |
| 10 | 23 | "designed to have" should read --designed to house-- |
| [57] Abstract (Title Page) | 10 | delete "and flange 32'" (second occurrence) |

Signed and Sealed this

Sixteenth Day of March, 1993

Attest:

STEPHEN G. KUNIN

Attesting Officer

Acting Commissioner of Patents and Trademarks